United States Patent
Melker

(10) Patent No.: US 7,258,120 B2
(45) Date of Patent: Aug. 21, 2007

(54) ENDOTRACHEAL TUBE APPARATUS AND METHOD FOR USING THE SAME TO REDUCE THE RISK OF INFECTIONS

(75) Inventor: Richard Melker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/157,003

(22) Filed: May 29, 2002

(65) Prior Publication Data

US 2004/0079376 A1    Apr. 29, 2004

(51) Int. Cl.
*A61M 16/00*    (2006.01)
(52) U.S. Cl. .............................. 128/207.14; 128/207.15
(58) Field of Classification Search ........... 128/207.14, 128/207.15, 207.17
See application file for complete search history.

(56) References Cited

U.S. PATENT DOCUMENTS

| | | | | |
|---|---|---|---|---|
| 3,087,493 | A | * | 4/1963 | Schossow ............... 128/207.15 |
| 3,173,418 | A | * | 3/1965 | Baran ..................... 128/207.15 |
| 4,022,219 | A | * | 5/1977 | Basta ..................... 128/207.14 |
| 4,327,720 | A | * | 5/1982 | Bronson et al. ........ 128/207.15 |
| 4,367,769 | A | * | 1/1983 | Bain .......................... 138/114 |
| 4,446,864 | A | * | 5/1984 | Watson et al. ......... 128/207.14 |
| 4,453,545 | A | * | 6/1984 | Inoue ..................... 128/207.15 |
| 4,688,568 | A | | 8/1987 | Frass et al. |
| 4,840,172 | A | | 6/1989 | Augustine et al. |
| 4,850,371 | A | * | 7/1989 | Broadhurst et al. ......... 600/532 |
| 5,029,580 | A | | 7/1991 | Radford et al. |
| 5,040,532 | A | | 8/1991 | Alfery |
| 5,065,755 | A | | 11/1991 | Klafta |
| 5,073,164 | A | | 12/1991 | Hollister et al. |
| 5,103,816 | A | * | 4/1992 | Kirschbaum et al. .. 128/207.14 |
| 5,125,893 | A | | 6/1992 | Dryden |
| 5,143,062 | A | | 9/1992 | Peckham |
| 5,167,622 | A | | 12/1992 | Muto |
| 5,197,463 | A | * | 3/1993 | Jeshuran ................. 128/207.14 |
| 5,359,999 | A | | 11/1994 | Kinsman |
| 5,392,772 | A | | 2/1995 | Zilbershtein |
| 5,499,625 | A | | 3/1996 | Frass et al. |
| 5,551,946 | A | | 9/1996 | Bullard |
| 5,588,424 | A | | 12/1996 | Insler et al. |
| 5,636,625 | A | * | 6/1997 | Miyagi et al. ......... 128/200.26 |
| 5,660,175 | A | | 8/1997 | Dayal |

(Continued)

OTHER PUBLICATIONS

Woske, Hans-Jurgen et al., *Ventilator-associated pneumonia in a surgical intensive care unit; epidemiology, etiology and comparison of three bronchoscopic methods for microbiological specimen sampling*, Critical Care 2001 5:167-173 http://www.biomedcentral.com/1364-8535/5/167.

(Continued)

*Primary Examiner*—(Jackie) Tan-Uyen Ho
*Assistant Examiner*—Darwin P Erezo
(74) *Attorney, Agent, or Firm*—Timothy H. Van Dyke; Beusse Wolter Sanks Mora & Maire

(57) ABSTRACT

Disclosed herein is a novel tube-in-tube endotracheal tube apparatus that allows for replacement or cleaning of an inner (first) tube without having to re-intubate the patient. The novel endotracheal tube apparatus enables the application of continuous suction or intermittent suction. The endotracheal device also serves to decrease the incidence of ventilator-associated pneumonia (VAP).

11 Claims, 4 Drawing Sheets

U.S. PATENT DOCUMENTS

| | | | |
|---|---|---|---|
| 5,665,052 A | | 9/1997 | Bullard |
| 5,722,391 A | * | 3/1998 | Rosenkoetter et al. .. 128/200.24 |
| 5,775,325 A | * | 7/1998 | Russo ................... 128/205.12 |
| 5,778,872 A | * | 7/1998 | Fukunaga et al. ..... 128/202.27 |
| 5,904,648 A | | 5/1999 | Arndt et al. |
| 5,954,636 A | | 9/1999 | Schwartz et al. |
| 6,237,597 B1 | | 5/2001 | Kovac |

OTHER PUBLICATIONS

Smulders, Kees et al., *A Randomized Clinical Trial of Intermittent Subglottic Secretion Drainage in Patients Receiving mechanical Ventilation*, Clinical Investigation in Critical Care, CHEST, Mar. 2002, 121:3 pp. 858-862.

Soloviev, M.V., *Comparison of Subglottic Suction Endotracheal Tubes*, Anesth Analg, 2002, 94; S-1-S-350; Abstract S-162.

Matsumoto, K., *Changes in Respiratory Mechanics During General Anesthesia With Mechanical Ventilation for Various Intraoperative Postures*, Anesth Analg, 2002, 94; S-1-S-350; Abstract S-163.

\* cited by examiner

ENDOTRACHEAL TUBE APPARATUS AND METHOD FOR USING THE SAME TO REDUCE THE RISK OF INFECTIONS

FIELD OF THE INVENTION

The present invention relates to a novel endotracheal tube apparatus and methods of using the same, and more specifically, a multiple lumen endotracheal tube device including a tube within a tube arrangement constructed to permit the inner tube to be removed from the outer tube by a removable connector and replaced by a new sterilized inner tube to reduce the risk of ventilator-associated pneumonia.

BACKGROUND OF THE INVENTION

Ventilation is the physiologic process which supplies oxygen to the body and removes carbon dioxide, a gaseous waste product. Normally, ventilation is provided from the cyclic flow of gas into and out of the lungs. The flow results from the contraction and relaxation of the diaphragm. Many surgical and critical care patients are unable to ventilate adequately, and ventilation must be provided mechanically using a mechanical ventilator and a single lumen endotracheal tube. An endotracheal tube (ETT) typically is comprised of a lumen or tube that is open at both ends, and has a comfort cuff or balloon positioned at one end. An ETT is positioned in the mid trachea whereby it acts as a conduit for gas from the ventilator to the lungs.

Patients who are critically ill or who have undergone surgical procedures require mechanical ventilation to sustain life. Patients that require mechanical ventilation for prolonged periods of time often develop a potentially fatal condition called ventilator-associated pneumonia or VAP. VAP is caused by bacteria build up in the moist environment on the ventilation tubing apparatus and infects the patient's lungs.

VAP is a major threat to the recovery of patients receiving mechanical ventilation, and is the most lethal infection in mechanically ventilated patients. VAP was the most frequent nosocomial infection aquired in ICUs in Europe, accounting for 45 percent of all infections. J L Vincent, D J Bihari, P M Suter, H A Bruining, J White, M H Nicolas-Chanoin, M Wolff, R C Spencer, M Hemmer: The prevalence of nosocomial infection in intensive care units in Europe. Results of the European Prevalence of Infection in Intensive Care (EPIC) Study. *J Am Med Assoc* 1995, 278: 639-644. The early and accurate diagnosis of VAP is difficult, but because of the increasing prevalence of multi-resistant pathogens in many ICUs; it constitutes an urgent challenge. It is especially difficult to distinguish VAP from other causes of fever and infection. A fatal outcome is frequently observed in patients who are mechanically ventilated for more than 48 hours. Several investigators have hypothesized that VAP has a direct causal influence on mortality. J Y Fagon, J Chastre, A J Hance, P Montravers, A Novara, C Gibert: Nosocomial pneumonia in ventilated patients: a cohort study evaluating attributable mortality and hospital stay, *Am J Med* 1993, 94: 281-288.

VAP can make a patient ill for a very long time or even cause death in critically ill patients, especially in infants and the elderly. In order to prevent or lessen the threat of VAP, health care professionals repeatedly re-intubate patients that require ventilation over long periods of time. Accordingly, there is a need in the art for an endotracheal tube apparatus designed for prolonged ventilation, which aids in preventing the VAP. Embodiments of the invention described herein utilize a unique tube in tube endotracheal tube design that provides for ventilation and suctioning. The tube in tube arrangement also allows for replacement of the ventilation tube of the endotracheal tube to prevent bacterial build up that can cause VAP.

Furthermore, the shape of the distal ends of current tracheal tubes can cause extensive damage to tracheal during intubation. A less intrusive tubal design would be desirous to reduce the injury and damage caused by the process of intubing a patient.

SUMMARY OF THE INVENTION

The present invention relates to a novel endotracheal tube apparatus including at least two tubes where one tube is inserted within the other tube to form a "tube-in-a-tube" structure. The subject ETT provides the ability to apply suction and be cleaned or replaced without damaging a patient's trachea.

It is an object of the present invention to provide an endotracheal tube apparatus that includes at least two tubes where the first tube is inserted into the second tube so that the first tube can be disposed of and replaced by another sterilized first tube to reduce the risk of ventilator-associated pneumonia.

It is another object of the present invention to provide an endotracheal tube apparatus having the distal ends of the second tube shaped such that the ends curve inward to reduce tracheal injury.

It is a further object of the present invention to provide an endotracheal tube apparatus having the distal ends of the second tube shaped such that the ends curve inward to direct secretions between the tubes to the suction port.

It is still a further object of the present invention to provide an endotracheal tube apparatus that is constructed of a hydrogel material to prevent adherence to tracheal tissue of the patient.

It is still another further object of the present invention to provide an endotracheal tube apparatus that is constructed of a hydrogel material inhibiting the build-up of bacteria which cause ventilator-associated pneumonia.

Still yet another aspect of the present invention relates to an endotracheal tube apparatus where the inner wall of the second tube or the outer wall of the first tube is provided with raised structures such as ribbed structures to form a channel between the first and second tube for suctioning to reduce the risk of ventilator-associated pneumonia. Preferably, the endotracheal tube apparatus has a multiple part connection at the proximal end. The multiple part connection is configured such that the inner (first) tube is responsible for ventilation and can be removed, cleaned, or disposed of and replaced while the patient remains intubated by the outer (second) tube. The subject ETT apparatus reduces the tissue damage to the trachea and surrounding areas, by overcoming the need for repeated re-intubation.

The foregoing has outlined some of the more pertinent objectives of the present invention. These objectives should be construed to be merely illustrative of some of the more prominent features and applications of the invention. Many other beneficial results can be attained by applying the disclosed invention in a different manner of modifying the invention as will be described.

It is to be understood that the foregoing general description and the following detailed description are exemplary and explanatory only and are not to be viewed as being restrictive of the present invention, as claimed. These and other objects, features and advantages of the present invention will become apparent after a review of the following detailed description of the disclosed embodiments and the appended claims. For example, although less preferred, those skilled in the art will appreciate that the subject apparatus could be configured such that suction occurs in the inner tube and ventilation occurs via the channel between the inner and outer tubes.

DESCRIPTION OF THE PREFERRED EMBODIMENTS

Figure 1:
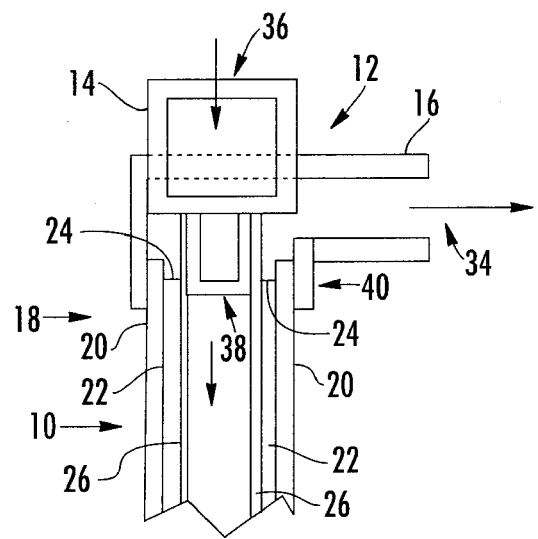
FIG. 1 illustrates a cross-sectional side view of an embodiment of the endotracheal tube apparatus showing the first and second connectors and the first and second tube arrangement according to the present invention.
Figure 1:
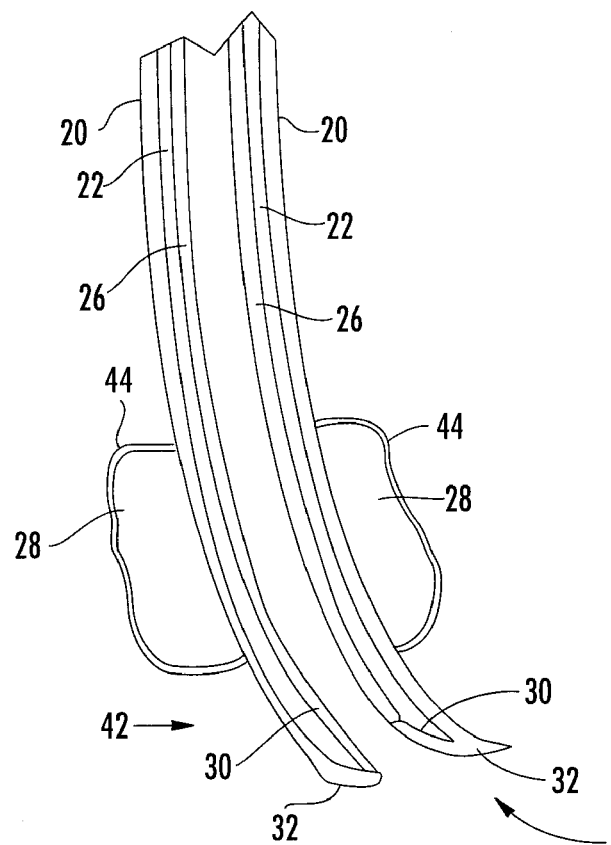
Figure 2:
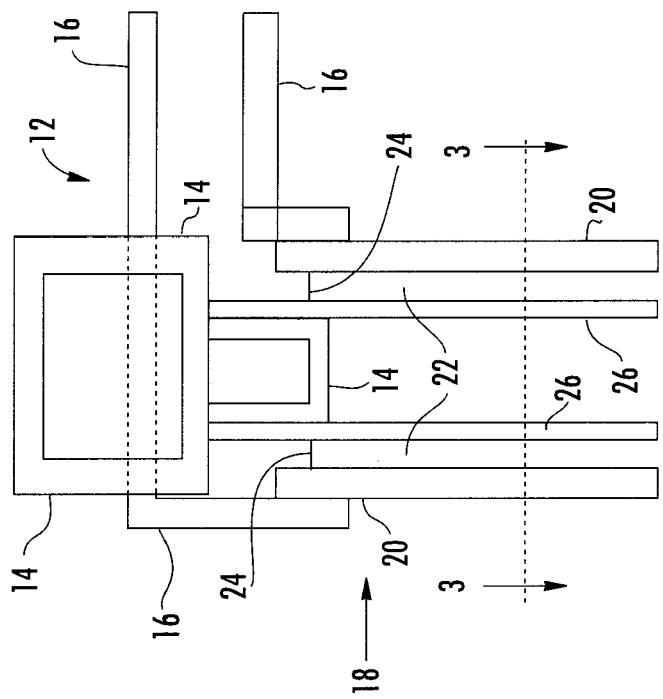
FIG. 2 illustrates an enlarged cross-sectional side view of the proximal end of the endotracheal tube apparatus showing the first and second connectors and where the first and second tubes are secured onto the connectors according to the present invention.

The present invention relates to a novel endotracheal tube apparatus 10 including at least two tubes 20 and 26 where the first tube 26 is inserted within the second tube 20 to form a "tube-in-a-tube" structure. The ETT preferably, but not necessarily, forms a concentric arrangement (shown in FIG. 1). At least two connectors are included in the subject invention where the first 14 and 16 second connectors are removeably attachable and dimensioned and configured to interconnect with one another. The second connector 16 may have two ports, one port 40 being dimensioned and configured to be attached to the proximal end of the second tube 20 and the other port 34 being removeably attached to a suction apparatus. The first connector 14 includes two ports, one port 38 being removeably attached to the proximal end 18 of the first tube and another port 36 being removeably attached to a ventilation device. The first connector 14 can be removeably attached from the second connector 16 during mechanical ventilation of a patient, and preferably, at least one inflatable cuff 28 to be inflated which is illustrated in FIGS. 1 and 2. As an alternative embodiment, the connections may be integral to the tubes as opposed to attached to the ends of the tubes. Either the outer wall of the first tube 26 or the inner wall of the second tube 20 may be provided with raised structures such as ribs, rod-like structures, bubbled structures, or the like 24 which form a first suction channel 22 between the walls of the two tubes 20 and 26.

The distal end 42 of the second tube 20 is preferably shaped so that the ends 32 curve inwards to reduce tracheal damage and to direct secretions into the first suction channel 22.

According to one embodiment, as shown in FIGS. 1 and 2, the present invention is an endotracheal tube apparatus 10 comprising at least two elongated tubes each having a proximal 18 and distal end 42, wherein a first tube 26 is removeably inserted inside the length of a second tube 20, the first tube 26 includes an inner and outer wall and the second tube 20 includes an inner and outer wall; and at least two connectors where the first 14 and second 16 connectors are removeably attachable and dimensioned and configured to interconnect with one another. The second connector 16 may comprise one or more ports. One port 40 being dimensioned and configured to be attached to the proximal end 18 of the outer tube 20 and another port 34 being removeably attached to a suction apparatus. The first connector 14 comprises two ports. One port 38 being removeably attached to the proximal end 18 of the first tube 26 and another port 36 being removeably attached to a ventilation device. The first connector 14 can be removeably attached from the second connector 16 during intubation of a patient.

In a preferred embodiment, the inner wall of the second tube 20 or the outer wall of the first tube 26 includes raised structures 24 to form a first suction channel 22 throughout the length of the apparatus between the elongated tubes 20 and 26. Alternatively, the raised structures 24 could be hollow, thus allowing distal airway pressure recording, suction, and illumination fibers.

The first tube 26 can be advanced or retracted with respect to proximal end 18 of elongated second tube 20. The first 26 and/or second 20 tubes of the endotracheal tube apparatus 10 are preferably constructed of a hydrogel-like material to reduce the risk of microbe build up, which may result in complications including ventilator-associated pneumonia. The first tube 26 and/or second 20 tube of the endotracheal tube are preferably constructed of or coated with a conventional pliable plastic such as polyvinyl chloride (PVC), polyurethane, fluroplastic, polyester, nylon, polypropylene and silicone plastic. However in a more preferred embodiment, the first tube 26 is constructed of a pliable plastic and the second tube is partially or completely constructed of a hydrogel material.

In a preferred embodiment, the distal end 42 of the second tube 20 is shaped so that the end 32 curves inwards to reduce tracheal injury and to direct secretions in the first suction channel 22. The endotracheal apparatus 10 also includes an inflatable cuff 28. There are many types and designs of inflatable cuffs or balloons that are known in the art and any of those can be incorporated into the present invention 10. Preferably, the inflatable cuff 28 can be secured onto the distal end 42 of the outer wall of the second tube 20. However, variations of cuff operations and integrations that are known in the art of endotracheal tube apparatuses can be incorporated into the present invention. The cuff may be made from a conventional elastomeric material such a latex, polyurethane, PVC, silicone rubber or silicone plastic. The leading and trailing ends of cuff may be attached to elongated member or tube at cuff attachment points using a conventional non-brittle, medical grade adhesive. The cuff preferably forms an elliptical shape when interior of the cuff is inflated via an air supply that communicate with an inflation lumen in the tube.

Figure 3:
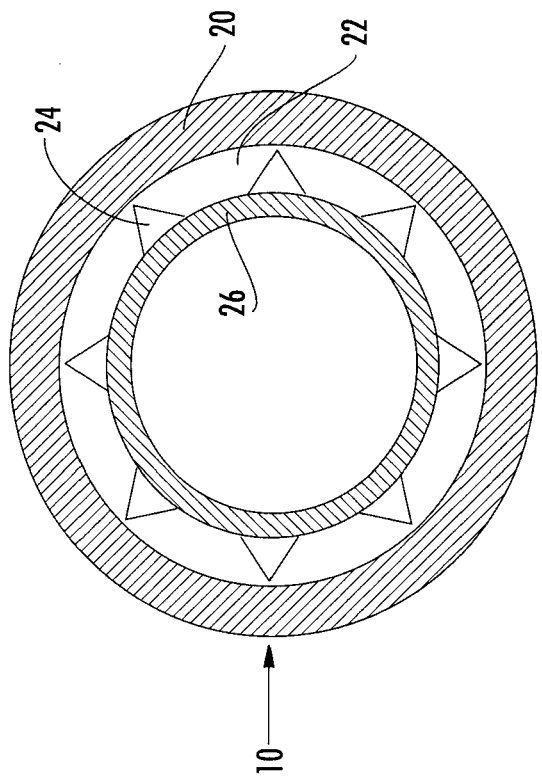
FIG. 3 is taken along the plane 3-3 of FIG. 2 as an enlarged cross-sectional view of a concentric tube arrangement showing a preferred arrangement of the raised structure(s) being formed as part of the outer wall of the first tube according to the present invention.
Figure 6:
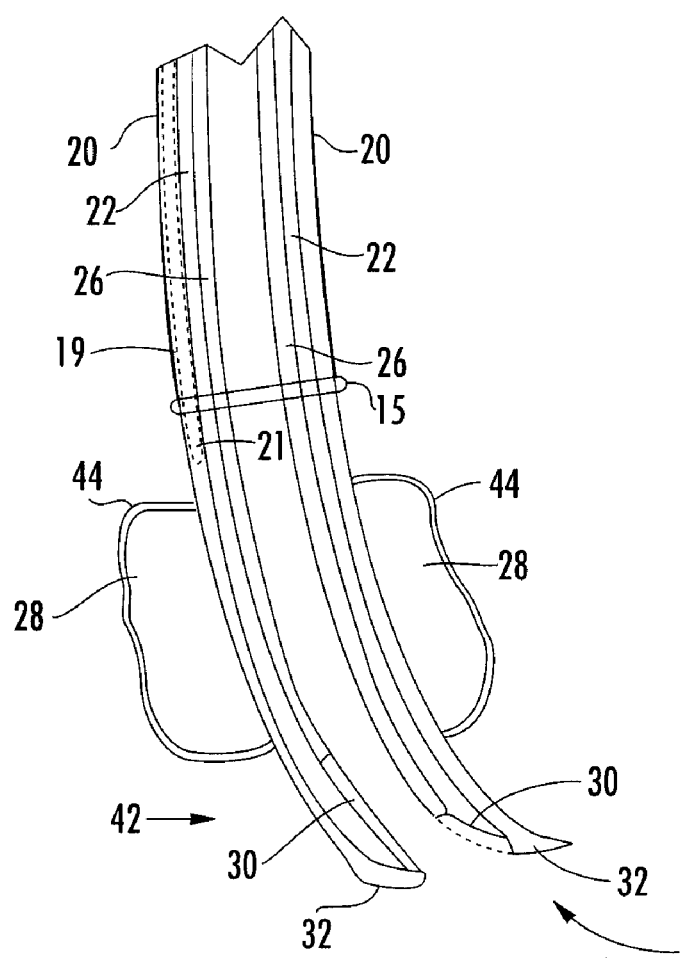
FIG. 6 illustrates an alternative embodiment of the present invention showing a second suction channel for subglottic secretion drainage during intubation according to the present invention.

The first suction channel 22 that is formed by the raised structures 24 on the wall which are secured or part of either the first tube 26 or second tube 20 and preferably runs throughout and between the entire length of both tubes 20 and 26 and allows for suction while the patient is intubated to remove gases and secretions and also to reduce the risk of ventilator-associated pneumonia. FIG. 3 shows a preferred embodiment of the endotracheal tube apparatus 10 having the ribbed structure(s) 24 as part of the outer wall of the first tube 26. When the first tube 26 with ribbed structure(s) 24 is removed, any bacterial build-up on the ribbed surface 24 would be removed and to allow suction. In an alternative embodiment, as shown in FIG. 6, at least one flexible outer sleeve 15 with a second suction channel 19 or second suction channel that is integrated into the endotracheal tubing extends along the outer tubing and opens through an orifice 21 above the inflated cuff 28. The second suction channel 19 is designed for subglottic secretion drainage during intubation. Suction as applied to the second suction channel 19 as an opening (not shown) at the proximal end of the subject endotracheal tube.

The connectors 14 and 16 of the endotracheal tube apparatus 10 are preferably formed by injection molding and may be removeably replaced while the patient is still intubated. The connectors 14 and 16 can be disposable or treatable through sterilization or other methods known in the art of cleaning medical equipment. The endotracheal tube apparatus 10 is constructed and structured to provide long term intubation of a patient needing ventilation by permitting the outer tube to remain in the patient's trachea while removing the first tube 26 to be cleaned or replaced by another first tube 26 which is reinserted through the length of the second tube 20 and reattached to the first connector 14 and is positively locked into the second connector 16.

Another embodiment of the present invention 10 includes a method of intubation which comprises inserting the distal end 42 of the second tube 20 into the lungs of a patient in need of ventilation. The first tube 26 is inserted into the second tube 20, and the first 14 and second 16 connectors are interconnected. A ventilator apparatus is connected to the first connector 14, and a suction device is connected to the second connector 16. Continuous or intermittent low vacuum suction is applied through the first suction channel 22. At a predetermined interval, the first tube 26 is removed and cleaned or replaced with another first tube 26 while patient is still intubated with the second tube 20.

The present invention 10 includes several aspects where the first 26 and second 20 tubes are constructed of a combination of a hydrogel and/or of conventional pliable plastic such as polyurethane, PVC, fluroplastic, polyester, nylon, polypropylene and silicone plastic, or any combination thereof.

The endotracheal tube apparatus 10 is constructed of materials that provide a hostile (non-ideal) surface for bacteria to form colonies. Since it take a considerably longer time for bacteria and other known infectious organisms to build-up on these hostile surfaces, long term intubation is safer. The distal portion 42 of the second tube 20 including the cuff 28 are manufactured of a hydrogel material which is not a suitable surface for bacteria to secrete substances that allow them to adhere, form colonies, and protect themselves from antibiotics. The cuff 28 also includes a hydrogel sleeve 44 to additional aid in reducing the risk of ventilator-associated pneumonia because it too provides a hostile surface for bacteria growth.

The operation of the endotracheal tube apparatus 10 starts with the insertion of either the second tube 20 or both first 26 and second 20 tubes into the lungs of a patient. A suction device is attached to one of the connectors 16 that function as a suction port where a continuous suction flow is supplied. The outer cuff 28 is inflated or the inner cuff (not shown) is inserted and inflated to a predetermined target area within the patient's lungs. The first suction channel 22 formed by the raised structures (see FIG. 3) permits gas to pass upwards to both expire unwanted $CO_2$ and to prevent further seeding of bacteria. The inner cuff (not shown) can be removed and the connector 14 and first tube 26 is removeably attached and the new first tube 26 is attached to the connector 14 and once again the connector 14 with new first tube 26 is positively locked into the other connector 16 while the endotracheal apparatus 10 is still intubated within the patient. The two removeably and positively locked connectors 14 and 16 and the first 26 and second 20 tubes may be in a concentric arrangement having a tube within a tube construction where the first tube 26 is removeably insertable while the endotracheal apparatus 10 (second tube 20) remains in place within the patient's lungs. The operation of the endotracheal tube apparatus 10 may vary in the order of steps and procedures described above.

Thus, it can be appreciated that the present endotracheal tube apparatus 10 is ideal for long term use. The average surgeon would find that the double lumen endotracheal apparatus 10 is much easier to utilize than the very difficult or impossible current endotracheal tubes. The present invention allows the average clinician to place the endotracheal tube apparatus 10 using average clinical skills in a timely, nonproblematic fashion with minimal trauma to the airway.

It will be readily understood by those skilled in the art that the general concept of the invention can be adapted for implementation into conventional double lumen endotracheal tubes. By way of background, in thoracic surgery, the chest wall is incised, the lung opened and the pleural space entered. As a result, the lung will collapse, and ventilation can escape. The ventilation to the non-operative lung must be isolated before opening the operative lung segment. The risk of patient harm exists if ventilation is not isolated before beginning thoracic surgery. This results from the escape of ventilation through the surgical lung opening. Isolation of ventilation is commonly required in medical patients. A portion of the lung can be diseased and requires isolation from mechanical ventilation. Conditions which require isolation are infection of the lung (pneumonia); bleeding in the lungs (hemoptysis); and a non-surgical opening into the pleural space (pneumothorax).

Double lumen endotracheal tubes are commercially available to achieve isolation of ventilation but are constructed to temporarily intubate a patient in need of ventilation. Double lumen endotracheal tubes available today are made of two endotracheal tubes fused together of unequal length. They incorporate two balloons, one balloon which envelopes the tracheal position of the two fused endotracheal tubes (the tracheal balloon) and a second which envelopes the longer portion and will extend into either the right or left mainstem bronchus (the bronchial balloon). A double lumen tube will isolate ventilation when positioned correctly with the longer portion in the right or left mainstem bronchus, and when both balloons are inflated.

There are disadvantages in using current double lumen endotracheal tubes. Double lumen endotracheal tubes are larger in diameter and longer than conventional endotracheal tubes and can damage the vocal chords and the nerves for the vocal chords. The left mainstem bronchus is difficult to enter with the longer portion. In patients where the normal airway anatomy is altered, the use of double lumen endotracheal tubes has caused patient harm. Due to the complexity and size, hypoxic brain damage has occurred because of the time needed to correctly place the device in the airway. Double lumen endotracheal tubes are only intended for temporary use because if left in place for long periods of time, they can cause damage to the tracheal bronchial tree including disruption.

Figure 4:
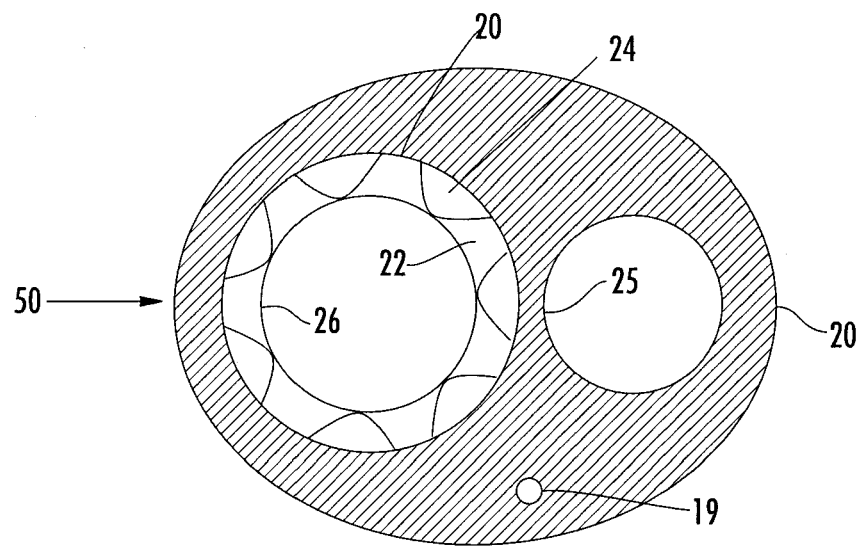
FIG. 4 is taken along the plane 4-4 of FIG. 5 and illustrates an enlarged cross-sectional view of an embodiment of double lumen endotracheal tube apparatus showing a preferred arrangement of the first and second lumens according to the present invention.
Figure 5:
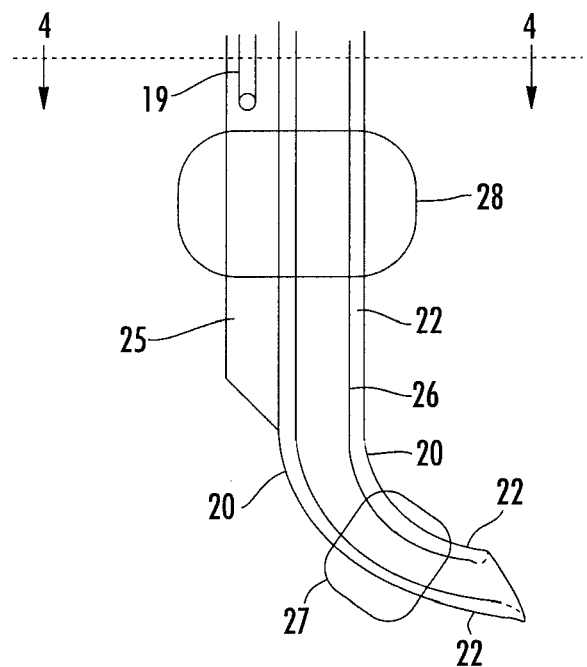
FIG. 5 illustrates a cross-sectional side view of an embodiment of the double lumen endotracheal tube apparatus showing a preferred arrangement of the first and second lumen according to the present invention.

According to an alternative embodiment, as shown in FIGS. 4 and 5, the subject invention is directed to a double lumen endotracheal tube 50 having at least two connectors are included in the subject invention where the first 14 and 16 second connectors are removeably attachable and dimensioned and configured to interconnect with one another. The second connector 16 may have two ports, one port 40 being dimensioned and configured to be attached to the proximal end of the second tube 20 and the other port 34 being removeably attached to a suction apparatus. The first connector 14 includes two ports, one port 38 being removeably attached to the proximal end 18 of the first tube and another port 36 being removeably attached to a ventilation device. The first connector 14 can be removeably attached from the second connector 16 during mechanical ventilation of a patient, and preferably, at least one inflatable cuff 28 to be inflated. The second tube 20 and removable first tube 26 make up the first lumen and extends into the bronchia. The first lumen also includes an inflatable cuff 27.

Either the outer wall of the first tube 26 or the inner wall of the second tube 20 may be provided with raised structures such as ribs, rod-like structures, bubbled structures, or the like 24 which form a first suction channel 22 between the walls of the two tubes 20 and 26. The distal end 42 of the second tube 20 is preferably shaped (e.g. by heating) so that the end 32 curves inwards to reduce tracheal damage and to direct secretions into the first suction channel 22. The second lumen 25 is a third suction channel that extends along the inside of the endotracheal tube apparatus 50 and opens directly above the second inflatable cuff 27 in the bronchia and below the first inflatable cuff 28 which deflates the lung by suction through a distal insert.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A double lumen endotracheal tube apparatus comprising:
    at least two elongated tubes each having a proximal and distal end, a first tube that is removeably inserted inside the length of a second tube at said proximal end, said first tube includes an inner and outer wall and said second tube includes an inner and outer wall, either said inner wall of said second tube or said outer wall of said first tube includes raised structure(s) to form a suction channel throughout the length of said elongated tubes to allow suction; said second tube forming a first lumen;
    at least two connectors comprising a first connector and a second connector which are positively locked and removeably attached to one another, the second connector having two ports, one port being configured for attachment to said proximal end of said second tube and another port being configured for attachment to a suction apparatus, the first connector having two ports, one being configured for attachment to said proximal end of said first tube and another port being configured for attachment to a ventilation device; wherein said endotracheal tube apparatus is configured such that when said first tube is positioned inside said second tube, when said first connector is attached to said first tube and to said ventilation device and when said second connector is attached to said second tube and said suction apparatus, inhalation and exhalation of said patient occurs through said first tube and suction occurs between said first tube and said second tube;
    a third tube defining a second lumen attached to or integral with said outer wall of said second tube, said third tube comprising a proximal and distal end and whose length is shorter than said second tube; and
    at least one first inflatable cuff surrounding said second tube, first tube, and said third tube to be inflated and positioned to permit a maximum contact area; and at least one second inflatable cuff surrounding said second and first tube, but not said third tube.

2. The endotracheal tube according to claim 1, wherein said second tube completely or partially constructed of a hydrogel material, said first tube is constructed of a conventional pliable plastic.

3. The endotracheal tube according to claim 2, wherein said second tube and first tube or any combination thereof are constructed of a conventional pliable plastic selected from the group consisting of polyurethane, PVC, fluroplastic, polyester, nylon, polypropylene and silicone plastic, and any combination thereof.

4. The endotracheal tube according to claim 1, further comprising additional suction channel that opens above said first inflated cuff to remove secretions accumulated during intubation.

5. The endotracheal tube according to claim 1, wherein said distal end of said second tube further comprises inward curves to reduce tracheal injury.

6. The endotracheal tube according to claim 1, wherein said second inflatable cuff is secured onto said distal end of said second tube.

7. The endotracheal tube according to claim 1, wherein said suction channel is to provide continuous suction while patient is intubated to remove gases and secretions to reduce the risk of ventilator-associated pneumonia.

8. The endotracheal tube according to claim 1, wherein said connectors and said elongated tubes are disposable or can be treated for use.

9. The endotracheal tube according to claim 1, wherein said connectors are made by plastic injection molding.

10. The endotracheal tube in claim 1, wherein said endotracheal tube apparatus is constructed to provide long term intubation of a patient needing ventilation.

11. A method of intubating a patient comprising obtaining an endotracheal tube comprising at least two elongated tubes each having a proximal and distal end, wherein a first tube is removeably positioned inside the length of a second tube, said first tube includes an inner and outer wall and said second tube includes an inner and outer wall; and
    at least two connectors comprising a first connector and a second connector that are removeably attachable and configured to interconnect with one another, said second connector having two ports, one port being configured for attachment to said proximal end of said second tube and another port being removeably attachable to a suction apparatus, said first connector having two ports, one being configured for attachment to said proximal end of said first tube and another port being removeably attachable to a ventilation device; and wherein said first connector is fashioned for detachment and attachment with said second connector during intubation of a patient; wherein said endotracheal tube apparatus is configured such that when said first tube is positioned inside said second tube, when said first connector is attached to said first tube and to said ventilation device and when said second connector is attached to said second tube and said suction apparatus, inhalation and exhalation of said patient occurs through said first tube and suction occurs between said first tube and said second tube;

positioning said endotracheal tube in a patient in need thereof;

detaching said first and second connectors;

removing said first tube out of said second tube;

treating or replacing said first tube;

inserting treated or replaced first tube into said second tube;

interconnecting said first and second connectors;

connecting a ventilator apparatus to said first connector;

connecting said suction apparatus to said second connector; and applying suction between said first tube and second tube while the patient is intubated.

* * * * *